United States Patent [19]
Ash

[11] Patent Number: 6,060,431
[45] Date of Patent: May 9, 2000

[54] FORMULATION AND PROCESS FOR THE SELECTIVE CONTROL OF BERMUDA AND OTHER GRASSES IN BENTGRASS, KENTUCKY BLUEGRASS, DICHONDERA, FINE FESCUE, TALL FESCUE, ANNUAL AND PERENNIAL RYEGRASS AND ST. AUGUSTINEGRASS TURFS AND ICEPLANT

[76] Inventor: David Ash, 1591 Princeton St., Madera, Calif. 93637

[21] Appl. No.: 09/084,075

[22] Filed: May 22, 1998

Related U.S. Application Data

[63] Continuation-in-part of application No. 08/709,765, Sep. 9, 1996, Pat. No. 5,756,425.

[51] Int. Cl.⁷ .................................................... A01N 43/40
[52] U.S. Cl. ........................................... 504/256; 504/258
[58] Field of Search ..................................... 504/258, 256

[56] References Cited

U.S. PATENT DOCUMENTS 5,428,000  6/1995  Innami et al. ........................... 504/104
5,686,391  11/1997 Crudden et al. ......................... 504/258
5,756,425  5/1998  Ash ......................................... 504/258

*Primary Examiner*—Jose' G. Dees
*Assistant Examiner*—Alton Pryor
*Attorney, Agent, or Firm*—Steins & Associates

[57] ABSTRACT

A Formulation and Process for the Selective Control of Bermuda and other grasses in Bentgrass, Kentucky Bluegrass, Dichondera, Fine Fescue, Tall Fescue, Annual and perennial Ryegrass and St. Augustinegrass turfs and Iceplant is disclosed. The disclosed process and formulation will not leave bare holes in the turf being treated. The disclosed formulation will not leave a chemical residue that is harmful to the turf under treatment. Said disclosed process may be employed as a preventive measure, such that bermudagrass and the like will be prevented from re-sprouting in the turf after the initial eradication. Also disclosed is a formulation and process that includes a biodegradable surfactant. Said surfactant is applyable to plants when the ambient temperature is in excess of eighty degrees Fahrenheit (80° F.) without harming the turf plants.

8 Claims, 2 Drawing Sheets

FORMULATION AND PROCESS FOR THE SELECTIVE CONTROL OF BERMUDA AND OTHER GRASSES IN BENTGRASS, KENTUCKY BLUEGRASS, DICHONDERA, FINE FESCUE, TALL FESCUE, ANNUAL AND PERENNIAL RYEGRASS AND ST. AUGUSTINEGRASS TURFS AND ICEPLANT

This application is a continuation-in-part of U.S. patent application Ser. No. 08/709,765, filed Sep. 9, 1996; now U.S. Pat. No. 5,756,425.

BACKGROUND OF THE INVENTION

1. Field of the Invention

This invention relates generally to the selective control of weeds in grasses and, more specifically, to a Formulation and Process for the Selective Control of Bermuda and other grasses in Bentgrass, Kentucky Bluegrass, Dichondera, Fine Fescue, Tall Fescue, Annual and perennial Ryegrass and St. Augustinegrass turfs and Iceplant.

2. Description of Related Art

Bentgrass (agrostis palustris) is the grass of choice for golf course putting greens, lawn bowling surfaces and similar areas. It is particularly suitable for these applications for a number of reasons. Bentgrass turf can be mowed very low and it has good resistance to wear. A bentgrass turf can also be repaired fairly quickly by either seed or sprig (i.e. cuttings). Bentgrass is particularly useful in sunny, hot areas, as it grows best in full sun. Bentgrass is a perennial grass that "creeps," or propagates by stolons, or above-ground runners (see FIG. 1). Bentgrass turf is typically very dense.

St. Augustinegrass (stenotaphrum secundatum) is a popular grass for lawns on the gulf coast of the United States and Southern California, among other areas. St. Augustinegrass, like bentgrass, can be mowed low and is also a perennial that propagates by stolons.

Similarly, Kentucky Bluegrass, Dichondera, Fine Fescue, Tall Fescue, Annual and perennial Ryegrass are widely grown as turf grasses around the world; they generally are durable perennial grasses that may or may not propogate by stolons.

Most turf areas comprise various types of grasses. Golf courses, for example, will use bentgrass for the greens only. The fairways typically comprise other grasses, such as bermudagrass, fescues or even bluegrass. Golf course roughs could be a variety of grasses, which are typically not controlled, since it is desirable that the roughs be more difficult to play on (by design). The difficulty created by these segregated grass areas is that golfers and golf carts track from one area to the next in the course of a golf game. It would be common for a golfer to walk from a fairway, through a rough, and back onto the fairway, before then proceeding to the green. It is in this way that the different grass types may be tracked from one area to the next. These other grass types may also be carried over to other areas by the wind, animals, or even by over-seeding. All of these carryover mechanisms are particularly troublesome to the maintenance of putting greens.

Extreme care is taken of these putting greens. The putting surfaces are fertilized, rolled flat and smooth, and cut at least daily (if not more). Even minute defects in the putting surface can cause major problems for the golfers. A common problem arises when grasses, other than bentgrass, sprout on a putting green. Bermudagrass and the others are not as dense or fine-bladed as bentgrass, and therefore they interrupt the otherwise smooth surface of the bentgrass green. Furthermore, when grasses such as bermudagrass sprout on a putting green, there has been no prior way to selectively remove the "weed," or unwanted grass, without also damaging the surrounding bentgrass.

Bermudagrass (cynodon dactylon) is a warm season perennial that creeps by stolons, like bentgrass and St. Augustinegrass, and also by rhizomes (below-ground runners) (see FIG. 2).

Historically, greens keepers have dealt with bermudagrass invasions of bentgrass turfs by either cutting them out of the putting green or by killing them with some type of chemical grass killer, such as "ROUNDUP." In either case, various serious problems arise. Cutting out or chemically killing the undesirable grass leaves holes in the putting greens that must then be re-planted with either shoots or seeds of bentgrass, since bentgrass is not amenable to sod-laying. Since either method removes all of the turf in the area of the unwanted grass, the entire section is left totally bare of living grass. Many times there is perfectly healthy bentgrass interweaved with the offending grass that is also destroyed by these two methods. If there was a means for killing only the offending grass, such as the bermudagrass, without harming the bentgrass, the section would not be left totally bare. The result would be a quicker recovery from "weed" grass removal. For the golfing industry, this would mean significant savings, since the current practice frequently mandates the decommissioning of the damaged putting green while the holes are being repaired, sometimes for weeks. Furthermore, the selective removal process could be used preventively, i.e. applications could be made periodically to kill the bermudagrass, etc. before it takes a strong hold within the putting green.

A further problem with chemically killing all of the turf surrounding the unwanted grass is that there is inevitably a residue of chemical left in the soil. This residual chemical must be allowed to be completely absorbed by the soil before new grass seed or sprouts can be planted in the bare spot. This may result in delays lasting several days, in addition to the time needed for the new bentgrass to fill in again. A method of killing unwanted grasses in a bentgrass green, such as bermudagrass, that does not leave a residue that is harmfull to bentgrass would eliminate this problematical situation.

Other problems exist with current chemical grass killers. Most of these prior chemical grass killers include a petroleum-based surfactant. These surfactants are included to insure that there is good coverage of, and adhesion to, the leaves (or blades) of the grasses being treated. Without the surfactant, the grass-killing chemical is more prone to run off of the grass leaves and into the soil, where it is much less effective at killing the grass, since most of these chemicals are designed to be absorbed by the leaves. The roots of the grass will not absorb the chemical as effectively or as quickly as the leaves.

One problem with petroleum-based surfactants is that when the ambient temperature exceeds eighty degrees Fahrenheit (80° F.), the surfactant tends to block the pores of the grass leaves. The blockage of the pores will prevent the leaves from absorbing nutrients, thereby damaging any grass plants where the petroleum-based surfactant has been applied. The result is that chemical grass killers containing these petroleum-based surfactants can only be safely applied during cool weather periods; this limits their utility severely, since it is typically desirable to apply the grass killing chemical during the hot summer months (i.e. when golf courses experience the most use).

Another problem with these petroleum-based surfactants is that petroleum is essentially a poison to most plant species, and therefore will by its nature harm the plants through its application. These petroleum-based surfactants should only be applied during periods when the grass is not in stress, i.e. not thirsting for water or hungry for nutrients. This limitation further narrows the utility of the chemical grass killers that include petroleum-based surfactants, because care must be taken not to apply them to plants that are in a weakened state. It would, therefore, be very beneficial to have a non-petroleum-based surfactant included with the grass-killing chemical, such as some sort of biodegradable material that does not harm the grass plants and therefore is not as limited in the ambient temperature range during which it can be safely applied.

These identical problems exist relative to Kentucky Bluegrass, Dichondera, Fine Fescue, Tall Fescue, and Annual and perennial Ryegrass Turfs as well as Iceplant, and a solution should also address these grasses and plants.

SUMMARY OF THE INVENTION

In light of the aforementioned problems associated with the prior methods and formulations, it is a primary object of the present invention to provide a Formulation and Process for the Selective Control of Bermuda and other grasses in Bentgrass, Kentucky Bluegrass, Dichondera, Fine Fescue, Tall Fescue, Annual and perennial Ryegrass and St. Augustinegrass turfs and Iceplant. It is a further object of the present process and formulation that holes bare of grass not be left in the turf being treated, and that any chemical residue remaining after treatment of the turf not be harmful to the turf. It is a further object that the present formulation and process be applyable as a preventive measure, such that bermudagrass, and the like will be prevented from re-sprouting in the turf after an initial eradication. The subject formulation may include a surfactant that is biodegradable and that is further able to be applied to plants when the ambient temperature is in excess of eighty degrees Fahrenheit (80° F.). Said surfactant should be virtually harmless to grass plants.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a Formulation and Process for the Selective Control of Bermuda and other grasses in Bentgrass, Kentucky Bluegrass, Dichondera, Fine Fescue, Tall Fescue, Annual and perennial Ryegrass and St. Augustinegrass turfs and Iceplant.

Figure 1:
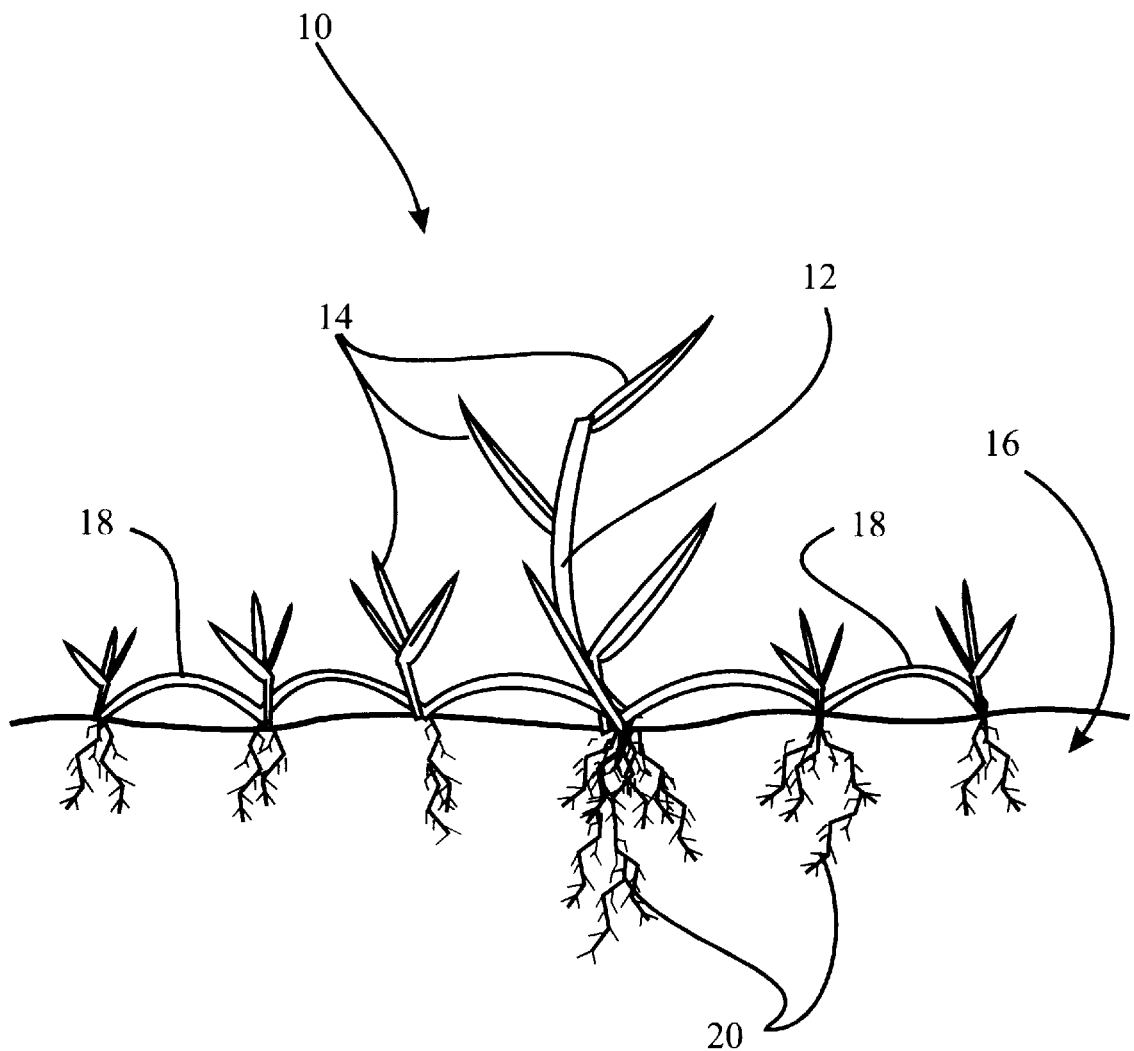
FIG. 1 is a side view of a typical bentgrass plant.

One may best appreciate the present invention by first considering FIG. 1. FIG. 1 depicts a typical bentgrass plant 10. As can be seen, a stem 12, including small blades or leaves 14 will propagate across soil 16 by above-ground stems, called stollens 18. The bentgrass plant acquires nutrients by absorption through the blades 14, or the roots 20. As is described below, the plant depicted in FIG. 1 is at three-leaf stage; the optimal growth stage for application of the treatment of the present invention.

Figure 2:
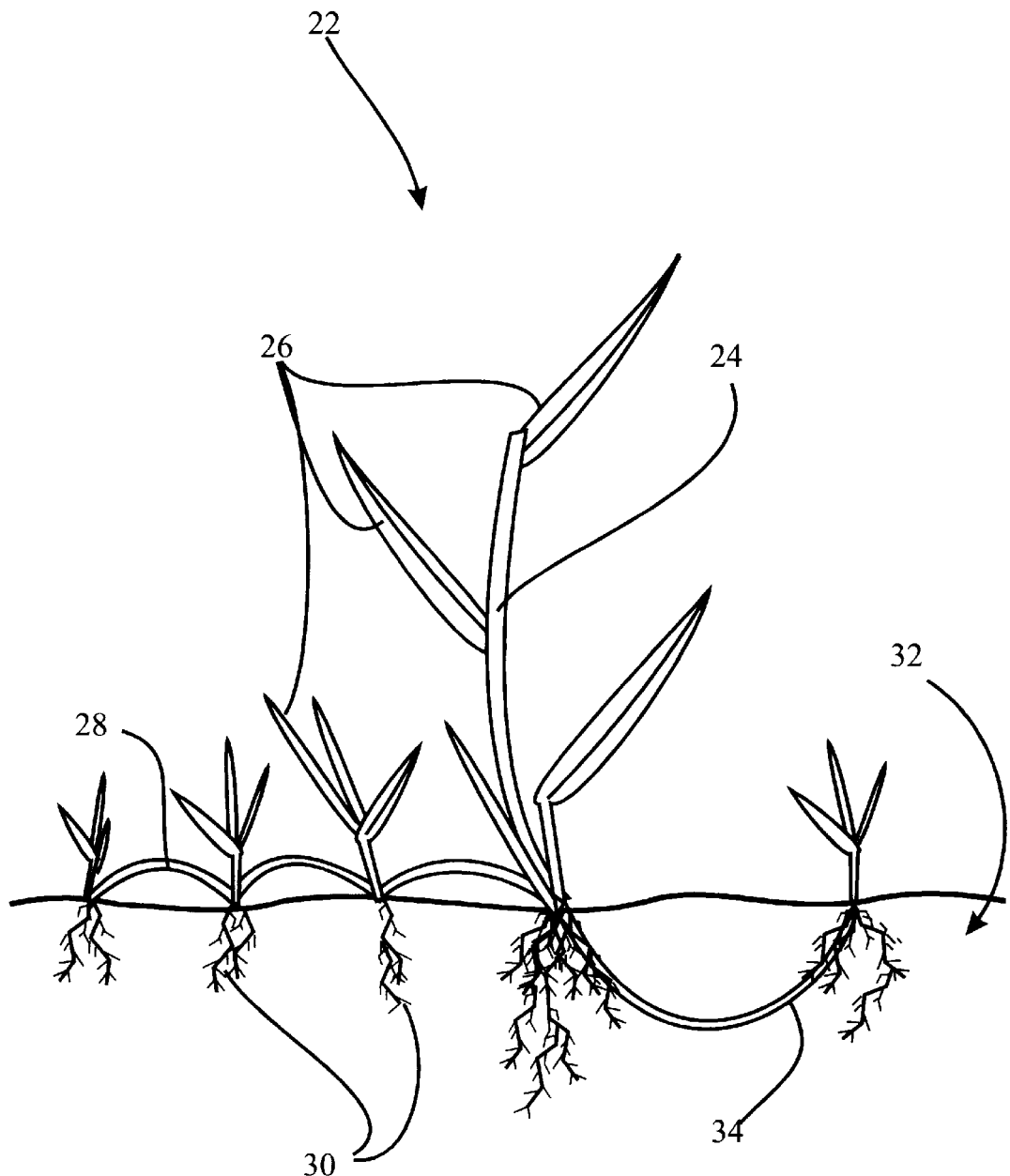
FIG. 2 is a side view of a typical bermudagrass plant.

Turning now to FIG. 2, one might appreciate the differences between bentgrass and bermudagrass. FIG. 2 depicts a typical bermudagrass plant 22. As with bentgrass, bermudagrass has a stem 24 with blades or leaves 26. It should be observed that bermudagrass leaves are proportionally larger than bentgrass leaves. Bermudagrass also has stollens 28 and roots 30. Additionally, bermudagrass is able to spread across soil 32 by below-ground stems, called rhizomes 34.

Now that the subject plants have been reviewed, we may discuss the details of the present invention. Fluazifop-P-butyl butyl(R)-2-[4-[[5-(trifluoromethyl)-2-pyridinyl] phenoxy] propanoate ("Fluazifop") is a widely available herbicide for the destruction of ornamental plants. It is marketed under the name "ORNAMEC" in a concentration of 6.75% by volume. If used as directed, ORNAMEC will destroy most ornamental grasses, including bentgrass, St. Augustinegrass, bermudagrass and poa annuagrass, among many others.

A critical aspect of the present formulation and process is the unexpected result that at certain concentrations and under certain conditions, fluazifop (and, similarly, butyl 2-[4-(5-trifluormethyl-2-pyridyloxy)phenoxy] proprionate) will selectively kill bermudagrass without damaging bentgrass or St. Augustinegrass. Specifically, one (1) teaspoon of 6.75% by volume fluazifop diluted in one (1) gallon of water has proven to selectively kill bermudagrass growing alone or within bentgrass turf.

Although it may not be fully understood why this result occurs consistently, it is believed that the core reason is different metabolistic rates between bentgrass and bermudagrass. Bentgrass is a non-disidual, cool season grass. As such, although it grows year around, it is not fertilized in the summer so that it will better tolerate the heat. Furthermore, bentgrass blades or leaves are relatively small when compared to bermudagrass, for example. Still further, much of the bentgrass foliage is typically absent, since the turf is cut very low. All of these factors are believed to contribute to the result that bentgrass exhibits very slow absorption rates through the leaves. St. Augustinegrass exhibits many of the same characteristics as bentgrass, and therefore can be expected to exhibit very slow leaf absorption rates also.

In contrast to bentgrass and St. Augustinegrass, bermudagrass is a warm season grass that goes dormant during the winter (i.e. after the first freeze). Once there has been three (3) to four (4) days of warm weather (ambient temperature 75–80° F.), the grass begins to grow again. Since the bermudagrass has a shortened growth season, it must absorb nutrients quickly in warm weather. In comparison to bentgrass and St. Augustinegrass, bermudagrass' rate of absorption in the summer months is much quicker. Furthermore, bermudagrass' blades are larger than bentgrass, and therefore have more surface area over which absorption can take place.

Testing has been conducted on all three strains of bentgrass (pentcross, seaside and creeping); the present formulation and process does not harm any of them if applied as directed.

Further included in the present formulation is a biodegradable surfactant. An example used here was a liquid soap, such as common household dishwashing liquid. As tested, approximately one (1) teaspoon of dishwashing liquid was added to one (1) gallon of the fluazifop/water mixture of the present invention. This surfactant promotes better coverage for the herbicide, but it also has further benefits. The surfactant leaves a visible residue on the grass plants after spraying; this aids in later locating where spraying has been done, and where it hasn't. More surprisingly, testing reveals that this surfactant is safe to spray at much higher ambient temperatures than petroleum-based surfactants. The formulation was safely applied to grass plants at ambient temperatures of up to 104° F.; more than twenty degrees above what is commonly recommended (for petroleum-based surfactants). This provides much more flexibility, and therefore utility, to the invention, since applications can be made through a much wider range of ambient temperatures.

Included herein is an example of a progression of testing that was performed. It is understood that not all grass combinations have been tested, however it is believed that other combinations of grasses that display different metabolistic rates, such as that between bermudagrass and bentgrass, exist. In such cases, results identical to those presented here could be expected. In particular, testing on bermudagrass in Kentucky Bluegrass, Dichondera, Fine Fescue, Tall Fescue, and Annual and perennial Ryegrass Turfs has had similar, successful results.

Test Progression

| Test # | Location # | Grass Type | Formulation (ounces chemical/gallon water) |
|---|---|---|---|
| I | 1 | bent with bermuda | P-1.0; F-1.75 |
|  | 2 | bent with bermuda |  |
| II | 3 | bent with bermuda | P-0.5; F-1.0 |
| III | 4 | bent | P-0.5; F-0.5 |
|  | 5 | bermuda |  |
| IV | 6 | bent | P-0.25; F-0.25 |
| V | 7 | bermuda | P-0.25; F-0.25 |
| VI | 8 | bent with bermuda | F-1.0 |
| VII | 9 | bent with bermuda | F-0.5 |
| VIII | 10 | bent with bermuda | F-0.17; S-0.17 |
| IX | 2 | bent with bermuda | F-0.17; S-0.17 |

"P" - 2-[1(ethoxyimino)butyl]-5-[2-ethylthio))propyl]-3-hydroxy-2-cyclohexen-1-one ("Poast")
"F" - butyl 2-[4-(5-trifluormethyl-2-pyridyloxy)phenoxy] proprionate ("Fluazifop")
"S" - Liquid soap, such as common dishwashing liquid Test Results

| Test # | Elapsed Time from Application (Days) | Grass Condition Bentgrass | Bermudagrass |
|---|---|---|---|
| I | 7 | some discoloration | some discoloration |
|  | 9 | dead | dead |
| II | 7 | discoloration | discoloration |
|  | 15 | dead | dead |
| III | 14 | dead | dead |
| IV | 21 | dead | — |
| V | 10 | — | dead |
| VI | 7 | discoloration | slight discoloration |
|  | 14 | dead | dead |
| VII | 7 | some discoloration | some discoloration |
|  | 14 | dead | dead |
| VIII | 7 | no discoloration | no discoloration |
|  | 9 | no discoloration | browning |
|  | 23 | no discoloration | dead |
| IX | 7 | some discoloration | undamaged |
|  | 14 | no discoloration | dead |

APPLICATION INSTRUCTIONS

The formulation of the present invention is a selective post-emergent. The treatment is most effective if the grass weed has reached 2 to 3 leaf stage prior to treatment. Irrigation should be halted at least approximately (4) hours prior to spraying. Irrigation should not be resumed for at least approximately two (2) hours after spraying. After spraying, the foliage should not be cut for at least approximately twelve (12) hours, to allow for adequate translocation of herbicide through the foliage.

The formulation can be pre-mixed or mixed from concentrate at the time of spraying. The grass weeds should be sprayed only enough to cover the foliate, but not such that run-off occurs. Repeat spraying may be necessary to obtain a complete kill in the event that some foliage was insufficiently developed to adequately absorb the herbicide.

Within one to one and one-half (1–1½) weeks after treatment, bermudagrass and the like should exhibit yellowing and browning. By three (3) weeks from treatment, bermudagrass and the like should be dead. Turf grass, such as bentgrass or St. Augustinegrass may display some discoloration from surfactant, however this will be removed with the first cutting.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A process for the selective control of Bermudagrass and the other warm season perennial grasses that creep by stolons and rhizomes in Bentgrass, Kentucky Bluegrass, Dichondera, Fine Fescue, Tall Fescue, Annual and perennial Ryegrass and St. Augustinegrass turfs and Iceplant, comprising the application of butyl 2-[4-(5-trifluormethyl-2-pyridyloxy)phenoxy] proprionate to said warm season perennial grass nestled adjacent to or within growths of said or said iceplant in an amount effective to kill said bermudagrass and the other warm season perennial grasses that creep by stolons and rhizomes but insufficient to damage said turfs or said iceplant.

2. The process of claim 1 which said compound comprises less than about 0.01 percent by volume.

3. The process of claim 2 which said compound further comprises a biodegradable surfactant.

4. The process of claim 3 comprising the steps of:
    watering the bermudagrass and the other warm season perennial grasses that creep by stolons and rhizomes;

waiting until the foliage of the bermudagrass and the other warm season perennial grasses that creep by stolons and rhizomes achieves 2 to 3 leaf stage, said waiting being coincident with said watering;

waiting about 4 hours from said last watering and after said foliage achieves said 2 to 3 leaf stage;

dispensing an adequate amount of said compound onto said foliage to cover said foliage without runoff;

waiting at least about 2 hours from said dispensing before watering the bermudagrass and the other warm season perennial grasses that creep by stolons and rhizomes; and waiting at least about 12 hours from said dispensing before cutting said foliage.

5. A process for the selective control of Bermudagrass and the other warm season perennial grasses that creep by stolons and rhizomes in Bentgrass, Kentucky Bluegrass, Dichondcra, Fine Fescue, Tall Fescue, Annual and perennial Ryegrass and St. Augustinegrass turfs and Iceplant, comprising treating said turf or said iceplant with a compound comprising butyl(R)-2-[4-[[5-trifluoromethyl)-2-pyridinyl]oxy]phenoxy]propanoate in an amount effective to kill said bermudagrass and the other warm season perennial grasses that creep by stolons and rhizomes but insufficient to damage said turfs or said iceplant.

6. The process of claim 5 in which said compound comprises less than about 0.01 percent by volume.

7. The process of claim 6 in which said compound further comprises a biodegradable surfactant.

8. The process of claim 6 comprising the steps of:

watering the bermudagrass and the other warm season perennial grasses that creep by stolons and rhizomes;

waiting until the foliage of the bermudagrass and the other warm season perennial grasses that creep by stolons and rhizomes achieves 2 to 3 leaf stage, said waiting being coincident with said watering;

waiting about 4 hours from said last watering and after said foliage achieves said 2 to 3 leaf;

dispensing an adequate amount of said compound onto said foliage to cover said foliage without runoff;

waiting at least about 2 hours from said dispensing before watering the bermudagrass and the other warm season perennial grasses that creep by stolons and rhizomes; and waiting at least about 12 hours from said dispensing before cutting said foliage.

* * * * *